United States Patent
Botzer et al.

(10) Patent No.: US 11,160,485 B2
(45) Date of Patent: Nov. 2, 2021

(54) PROPAGATION MAP OF A HEART CHAMBER WITH AREAS DEMONSTRATING FRACTIONATED ELECTROGRAMS

(71) Applicant: BIOSENSE WEBSTER (ISRAEL) LTD., Yokneam (IL)

(72) Inventors: Lior Botzer, Timrat (IL); Eliyahu Ravuna, Kiryat Ata (IL); Netta Dov, Ramat Ishay (IL); Guy Wekselman, Tel Aviv (IL); Simon Rivron, Rouen (FR)

(73) Assignee: Biosense Webster (Israel) Ltd., Yokneam (IL)

( * ) Notice: Subject to any disclaimer, the term of this patent is extended or adjusted under 35 U.S.C. 154(b) by 90 days.

(21) Appl. No.: 16/837,196

(22) Filed: Apr. 1, 2020

(65) Prior Publication Data
US 2021/0307634 A1   Oct. 7, 2021

(51) Int. Cl.
| | |
|---|---|
| A61B 5/343 | (2021.01) |
| A61B 5/339 | (2021.01) |
| A61B 5/364 | (2021.01) |
| A61B 5/333 | (2021.01) |
| A61B 5/346 | (2021.01) |

(52) U.S. Cl.
CPC .............. *A61B 5/339* (2021.01); *A61B 5/333* (2021.01); *A61B 5/343* (2021.01); *A61B 5/346* (2021.01); *A61B 5/364* (2021.01)

(58) Field of Classification Search
None
See application file for complete search history.

(56) References Cited

U.S. PATENT DOCUMENTS

| | | | |
|---|---|---|---|
| 8,838,216 B2 | 9/2014 | Francis | |
| 9,050,011 B2 | 6/2015 | Rubinstein | |
| 9,629,567 B2 * | 4/2017 | Porath | A61B 5/287 |

(Continued)

FOREIGN PATENT DOCUMENTS

EP   3750478 A1   12/2020

OTHER PUBLICATIONS

European Search Report for corresponding EPA No. 21166138.4 dated Aug. 25, 2021.

(Continued)

*Primary Examiner* — Kennedy Schaetzle

(57) ABSTRACT

A method includes storing an anatomical map of at least a portion of a surface of a heart. Respective electrogram (EGM) signal amplitudes measured at respective positions on the surface of the heart are stored. Based on the on the EGM signal amplitudes, defined are: one or more first regions of the surface in which the EGM signal amplitudes are fractionated, and one or more second regions of the surface in which the EGM signal amplitudes are non-fractionated. A first surface representation is generated for the fractionated EGM signal amplitudes in the first regions. Propagation times are extracted from the non-fractionated EGM signal amplitudes in the second regions, and a second surface representation of the propagation times is derived. The first and second surface representations of the respective first and second regions of the surface are simultaneously presented, overlaid on the anatomical map.

18 Claims, 3 Drawing Sheets

(56) References Cited

U.S. PATENT DOCUMENTS

| | | | |
|---|---|---|---|
| 2007/0073179 A1* | 3/2007 | Afonso | A61B 5/349 |
| | | | 600/523 |
| 2009/0192393 A1 | 7/2009 | Hayam | |
| 2010/0280399 A1 | 11/2010 | Francis | |
| 2011/0144510 A1* | 6/2011 | Ryu | A61B 5/283 |
| | | | 600/509 |
| 2012/0184863 A1* | 7/2012 | Harlev | G16H 15/00 |
| | | | 600/509 |
| 2014/0005563 A1 | 1/2014 | Ramanathan | |
| 2014/0200429 A1 | 7/2014 | Spector | |
| 2017/0360319 A1 | 12/2017 | Hagfors | |
| 2020/0196890 A1* | 6/2020 | Cohen | A61B 5/7425 |
| 2021/0161426 A1* | 6/2021 | Ziv-Ari | A61B 5/6859 |

OTHER PUBLICATIONS

Abdi Bahareh et al., "Local Activation Time Estimation in Fractionated Electrograms of Cardiac Mappings", 2019 $41^{st}$ Annual International Conference of the IEEE Engineering in Medicine and Biology Society, Jul. 23, 2019, pp. 285-288, XP033624595.

Vishal Luther et al., "A Prospective Study of Ripple Mapping in Atrial Tacycardias: A Novel Approach to Interpreting Activation in Low-Voltage Areas", Circulation: Arrhythmia and Electrophysiology, vol. 9, No. 1, Jan. 12, 2016.

* cited by examiner

PROPAGATION MAP OF A HEART CHAMBER WITH AREAS DEMONSTRATING FRACTIONATED ELECTROGRAMS

FIELD OF THE INVENTION

The present invention relates generally to electrophysiological mapping, and particularly to visualization of cardiac electrophysiological maps.

BACKGROUND OF THE INVENTION

Electrophysiological (EP) cardiac mapping may use visualizations methods previously proposed in the patent literature, to ease an interpretation of an EP map. For example, U.S. Pat. No. 8,838,216 describes a method of generating a model of a cardiac surface having a plurality of images representing electrogram voltages for a plurality of measured points within a heart. The method comprises measuring an electrogram voltage at a plurality of points within a heart, generating a first model of a cardiac surface of the heart, generating an image representing each electrogram voltage, each image having a characteristic representative of the electrogram voltage, and generating a further model of a cardiac surface. The images representing the electrogram voltages protrude from the further model of the cardiac surface at points on the further model corresponding to the points at which the electrogram voltages were measured. There is also disclosed an apparatus for generating a model of a cardiac surface.

As another example, U.S. Patent Application Publication 2009/0192393 describes software and apparatus to automatically detect and map ganglionated plexi that are found within areas of complex fractionated atrial electrograms (CFAE) in cardiac chambers when atrial fibrillations (AFib) occurs. Electrogram signals are analyzed to count the number of complexes whose amplitude and peak-to-peak intervals meet certain criteria. Functional maps indicating a spatial distribution of the ganglionated plexi and the relative numbers of complex fractionated electrograms are produced for display.

U.S. Patent Application Publication 2014/0005563 describes a method for visualization of electrophysiology information that can include electroanatomic data representing electrical activity on an anatomic region within a patient's body over a time period. An interval within the time period is selected in response to a user selection. A visual representation of physiological information for the user selected interval can be generated by applying at least one analysis method to the electroanatomic data. The visual representation can be spatially overlaid on a graphical representation of the anatomic region within the patient's body. In one embodiment of the invention, degrees of fractionations can be displayed spatially as 3D complex fractionated electrogram maps. Lowest to highest degrees of fractionations can be visually identified by a colormap.

SUMMARY OF THE INVENTION

An embodiment of the present invention provides a method, including storing an anatomical map of at least a portion of a surface of a heart. Respective electrogram (EGM) signal amplitudes measured at respective positions on the surface of the heart are stored. Based on the on the EGM signal amplitudes, defined are: one or more first regions of the surface in which the EGM signal amplitudes are fractionated, and one or more second regions of the surface in which the EGM signal amplitudes are non-fractionated. A first surface representation is generated for the fractionated EGM signal amplitudes in the first regions. Propagation times are extracted from the non-fractionated EGM signal amplitudes in the second regions, and a second surface representation of the propagation times is derived. The first and second surface representations of the respective first and second regions of the surface are simultaneously presented, overlaid on the anatomical map.

In some embodiments, the method further includes generating a third surface representation, for signals which are neither defined as fractionated, nor definable in terms of a propagation time.

In an embodiment, generating the first surface representation for the fractionated EGM signal amplitudes includes selecting a subset of the fractionated EGM signal amplitudes and generating the surface for the subset.

In some embodiments, the first surface representation includes a geometric shape protruding from the surface. In some embodiments, the protruding geometric shape includes one of ripples and bars.

In an embodiment, the second surface representation includes a color scale.

In some embodiments, the propagation times include local activation time (LAT) values.

In an embodiment, the method further includes assigning a local activation time (LAT) value to an EGM signal even though the EGM signal is fractionated, and generating for the fractionated EGM signal a third surface representation that visualizes the third surface representation.

In another embodiments the propagation times include cycle-length values.

There is additionally provided, in accordance with another embodiment of the present invention, a system including a memory and a processor. The memory is configured to store an anatomical map of at least a portion of a surface of a heart, and store respective electrogram (EGM) signal amplitudes measured at respective positions on the surface of the heart. The processor is configured to (i) define, based on the on the EGM signal amplitudes, one or more first regions of the surface in which the EGM signal amplitudes are fractionated, and one or more second regions of the surface in which the EGM signal amplitudes are non-fractionated, (ii) generate a first surface representation for the fractionated EGM signal amplitudes in the first regions, (iii) extract propagation times from the non-fractionated EGM signal amplitudes in the second regions, and derive a second surface representation of the propagation times, (iv) and simultaneously present the first and second surface representations of the respective first and second regions of the surface, overlaid on the anatomical map.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
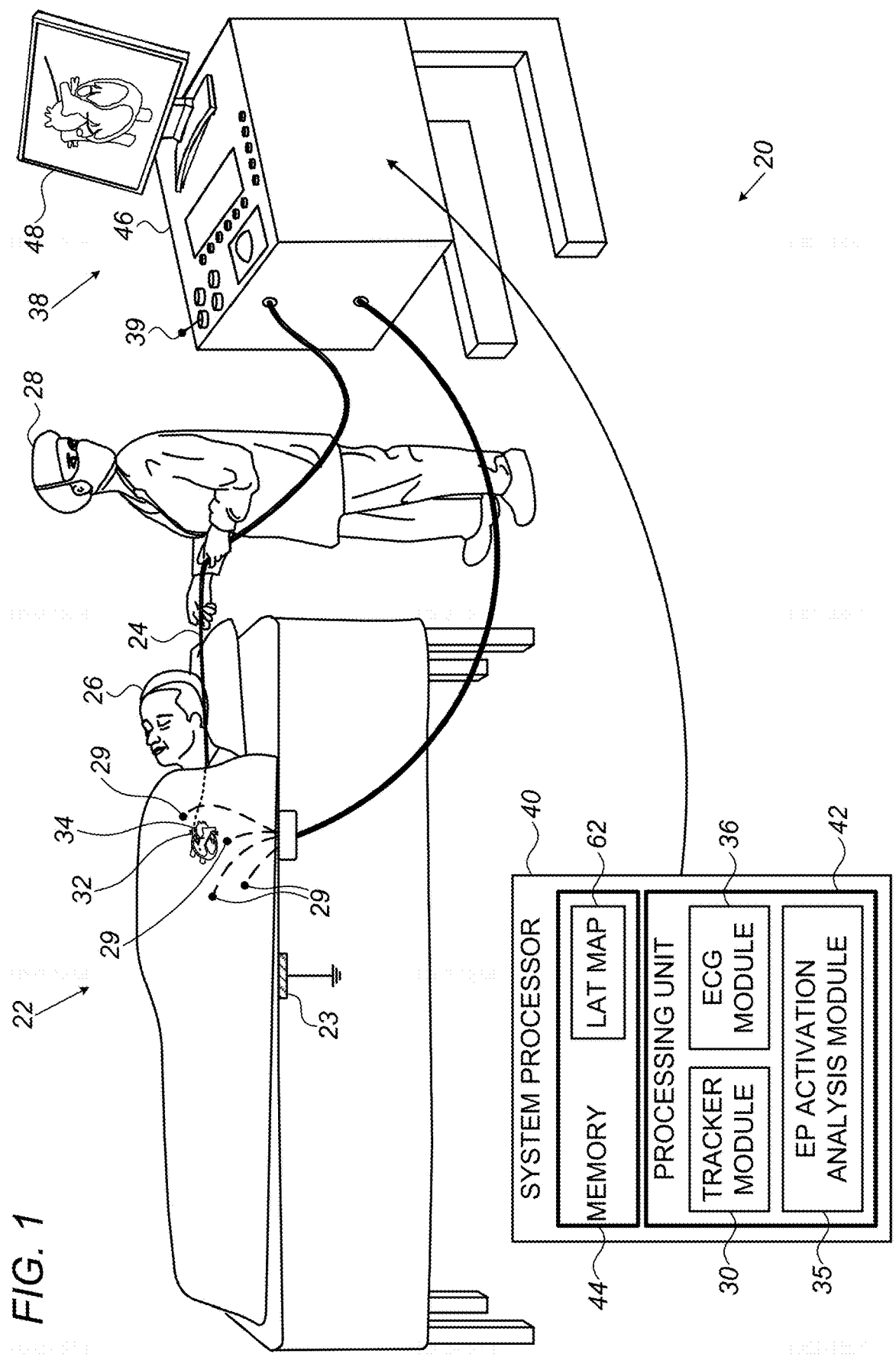
FIG. 1 is a schematic, pictorial illustration of a catheter-based cardiac navigation and electrophysiological (EP) signal analysis system, in accordance with an exemplary embodiment of the present invention.

Cardiac arrhythmia is a class of clinical conditions in which the heartbeat is irregular. Included among these cardiac arrhythmia conditions are important classes such as types of ventricular tachycardia, atrial tachycardia, as well as types of fibrillation.

In order to characterize cardiac arrhythmia of a patient, a catheter-based electrophysiological (EP) mapping system may be used to generate an EP map of least part of the heart of the patient, such as an EP map of a cardiac chamber. In a typical catheter-based EP mapping procedure, a distal end of a catheter, which comprises one or more sensing-electrodes, is inserted into the cardiac chamber to sense EP signals. As a physician operating the system moves the distal end inside the cardiac chamber, the EP-mapping system acquires EP signals at various locations on the inner surface of the cardiac chamber, as well as the respective positions of the distal end. Based on these acquired signals, a processor of the mapping system generates the required EP map, such as a map comprising local activation times (LAT) overlaid on an anatomical map of the cardiac chamber.

An LAT map typically comprises regions showing normal cyclic electric activity (e.g., sinus rhythm), regions that show abnormal rapid cyclic electric activity (e.g., rotors) and regions that show complex fragmented electrograms in pathological tissues. However, in time, periods of normal electrograms, episodes of rapid-cycle electrograms, and occurrences of complex fragmented electrograms can be observed in regions largely demonstrating sinus rhythm and in tachycardia.

An LAT map may thus indicate the occurrence of abnormal, yet well-defined, propagation characteristics of EP signals. For example, an LAT map may indicate the reentry of tachycardia (RT) by showing regions in which the EP activation wave propagates in closed loops with well-defined, yet pathological, cycle lengths (e.g., times between consecutive peaks in an electrogram).

In some cases, however, an EP abnormality can be manifested by episodes during which the electrograms are fractionated (e.g., made of irregular patterns such as bursts of highly rapid deflections of the signal), making a time which the EP wave passes under an acquisition electrode undefinable (or actually not occurring). In the present context, the term "fractionated electrogram" means an a-periodic electrogram having no characteristic cycle time and, in some cases, not even having a definable peak to derive a LAT value for.

For locations exhibiting fractionated electrograms, an EP propagation map based on LAT values or cycle times is practically useless, since it is difficult to calculate a meaningful LAT value from such electrogram signals. Still, it was found that the occurrence of fractionated electrograms is clinically significant, and therefore their presentation on an EP map is deemed important for accurate assessment of an underlying EP pathology.

One possible way to integrate fractionated signals in an EP map is to use a time dependent "ripple" map, in which the instantaneous EP amplitudes are shown as a function of time, for example, by being presented as time-varying bars protruding from the heart chamber surface. In such a presentation, the length (height) of each bar is indicative of the voltage measured at the corresponding location on the cardiac chamber surface at a given time. However, applying ripple mapping to an entire cardiac chamber is typically computationally-intensive and visually too complex to interpret, and moreover may compromise clarity of presentation of other important EP information (e.g., LAT information), as the other information might be omitted or obscured in such a map.

To overcome the above challenges, exemplary embodiments of the present invention that are described hereinafter separate the cardiac chamber map into fractionated and non-fractionated areas, and incorporate two different types of display into the map simultaneously. In some exemplary embodiments, a hybrid-representation EP map is provided, in which, using different graphical representations, well-defined EP propagation properties (e.g., LAT values) and fractionated EP signal amplitudes are respectively overlaid on the cardiac anatomy without either of them obscuring the other. The process typically follows the steps in which a processor carries out the following:

1. Generates an EP map comprising an anatomical map encoded with one or more first regions of fractionated EP activity and one or more second regions of well-defined EP activity, and delineates the different regions over the anatomy using data analysis methods such as deep learning or clustering. The one or more first regions and one or more second regions of the surface are defined, using a processor, based on the on the electrogram (EGM) signal amplitudes, as described below. The processor then generates a first surface representation for the fractionated EGM signal amplitudes in the first regions, extracts propagation times from the non-fractionated EGM signal amplitudes in the second regions, and derives a second surface representation of the propagation times. Finally, the processor presents simultaneously the first and second surface representations of the respective first and second regions of the surface, overlaid on the anatomical map.

2. When a user requests a propagation map, the processor displays the traditional propagation map, e.g., such as derived from LAT values, on non-fractionated areas, and, simultaneously, displays a ripple map on fractionated areas.

A traditional propagation map consists of a moving highlight, hue, color or some other visual indication that propagates according to the LAT values of the points. Generally, each point has one LAT value, however, some points may also have multiple LAT values, for example a double potential point may have two LAT values. If the system is designed to have at most one LAT value on each point, the traditional propagation map highlights each point at most once. If the system is designed to assign multiple LAT values to some points, the traditional propagation map may highlight some points multiple times.

In another exemplary embodiment, the processor generates a third surface representation, for signals which are neither defined as fractionated, nor definable in terms of a propagation time, such as to present double potentials.

In yet another exemplary embodiment, the processor selects only a subset of the signal it deemed fractionated, to represent by the first surface representation.

In some cases, even though a certain EGM signal is fractionated, it is still possible to approximate or otherwise assign it a LAT value. In an exemplary embodiment, the processor is further configured to generate a different surface representation for such fractionated EGM signals. In this exemplary embodiment, fractionated signals can be represented by ripple and/or LAT-value-based map representations.

The disclosed hybrid-representation EP map is dynamic in essence and capable of showing areas demonstrating time-dependent fractionated and non-fractionated electrogram (EGM) behavior, for example, in a video mode of the hybrid map.

By using different graphical means (e.g., ripples and color scaling) to display fractionated and non-fractionated EGM signatures on cardiac anatomy, the disclosed hybrid-representation EP mapping technique may improve the diagnostic value of catheter-based EP mapping procedures.

System Description

FIG. 1 is a schematic, pictorial illustration of a catheter-based cardiac navigation and electrophysiological (EP) signal analysis system 20, in accordance with an exemplary embodiment of the present invention. System 20 may be configured to analyze substantially any physiological parameter or combination of such parameters. In the description herein, by way of example, the signals analyzed are assumed to be intra-cardiac electrograms (EGM) and/or extra-cardiac (body surface) electrocardiogram (ECG) potential-time relationships. In order to fully characterize such relationships, the signals at various locations need to be referenced in time to each other, such as is done during local activation time (LAT) map generation. The time referencing is accomplished by taking measurements relative to a reference-time (e.g., an instance in time), such as the beginning of each QRS complex of an ECG reference signal (i.e., the beginning of every heartbeat). In an exemplary embodiment, the reference signal is received from a catheter placed in the coronary sinus. A method for generating an LAT map is described in U.S. Pat. No. 9,050,011, whose disclosure in fully incorporated herein by reference.

For simplicity and clarity, the following description, except where otherwise stated, assumes an investigative procedure wherein system 20 measures actual electrical activity of a heart 34, using a probe 24. A distal end 32 of the probe is assumed to have electrodes 22. The measured signals are used, among other usages, for creating an LAT map of at least part of the wall tissue of heart 34 of a patient 26.

Typically, probe 24 comprises a catheter which is inserted into the body of patient 26 during a mapping procedure performed by a physician 28 using system 20. During the procedure a grounding electrode 23 is assumed to be attached to patient 26. In addition, electrodes 29 are assumed to be attached to the skin of patient 26, in the region of heart 34.

In an exemplary embodiment, probe 24 acquires EGMs as it being is moved over a portion of the heart chamber. Some of the features in the measured EGM traces are annotated at the moment that an aberrant EP activation wave passes under a catheter electrode. At these instances probe 24 location is recorded as well.

System 20 may be controlled by a system processor 40, comprising a processing unit 42 communicating with a memory 44. In some embodiments, a memory 44, which is included in system processor 40, stores an LAT and/or voltage map 62 of at least part of wall tissue of heart 34 of patient 26. Processor 40 is typically mounted in a console 46, which comprises operating controls 38, typically including a pointing device 39 such as a mouse or trackball, used by physician 28 to interact with the processor.

Processor 40 (specifically processing unit 42) runs software, comprising a probe tracker module 30, an ECG module 36, and an EP activation analysis module 35, to operate system 20 and/or for EP activation analysis module 35 to run the at least part of disclosed analysis (using, for example, LAT or adjusted LAT maps 62 stored in memory 44) so as to model arrhythmia.

ECG module 36 is coupled to receive actual electrical signals from electrodes 22 and electrodes 29. The module is configured to analyze the actual signals and may present the results of the analysis in a standard ECG format, typically a graphical representation moving with time, on a display 48.

Probe tracker module 30 typically tracks the location of distal end 32 of probe 24 within the heart 34 of patient 26. The tracker module 30 may use any method for location tracking probes known in the art. For example, module 30 may operate a magnetic-field based location tracking subsystem. For simplicity, components of such a sub-system are not shown in FIG. 1.

Alternatively, or additionally, tracker module 30 may track probe 24 by measuring impedances between electrode 23, electrodes 29, and electrodes 22, as well as the impedances to other electrodes which may be located on the probe. In this case electrodes 22 and/or electrodes 29 may provide both ECG and location tracking signals. The Carto3® system, produced by Biosense-Webster (Irvine, Calif.), uses both magnetic field location tracking and impedance measurements for location tracking.

Using tracker module 30, processor 40 is able to measure locations of distal end 32. In addition, using both tracker module 30 and ECG module 36, the processor is able to measure locations of the distal end, as well as LATs of the actual electrical signals detected at these particular locations. As indicated above, electrical tracking signals from an individual electrode 22 can be integrated with the magnetic tracking signals so that the location of each electrode is recorded. Such a combined (i.e., magnetic/electric) tracking system and method, is the electric Advanced Current Location (ACL) system, implemented in various medical applications, for example, in the CARTO™ system, produced by Biosense-Webster Inc., and is described in detail in U.S. Pat. No. 8,456,182 whose disclosure is incorporated herein by reference.

Results of the operations performed by processor 40 are presented to physician 28 on display 48, which typically presents a graphic user interface to the physician, a visual representation of the ECG signals sensed by electrodes 22, and/or an image or map of heart 34 while it is being investigated.

The software run by processor 40 may be downloaded to processor 40 in electronic form, over a network, for example, or it may, alternatively or additionally, be provided and/or stored on non-transitory tangible media, such as magnetic, optical, or electronic memory. In particular, processor 40 runs a dedicated algorithm that enables processor 40 to perform the disclosed steps, as described below.

Fractionated Electrogram (EGM) Signals

Figure 2:
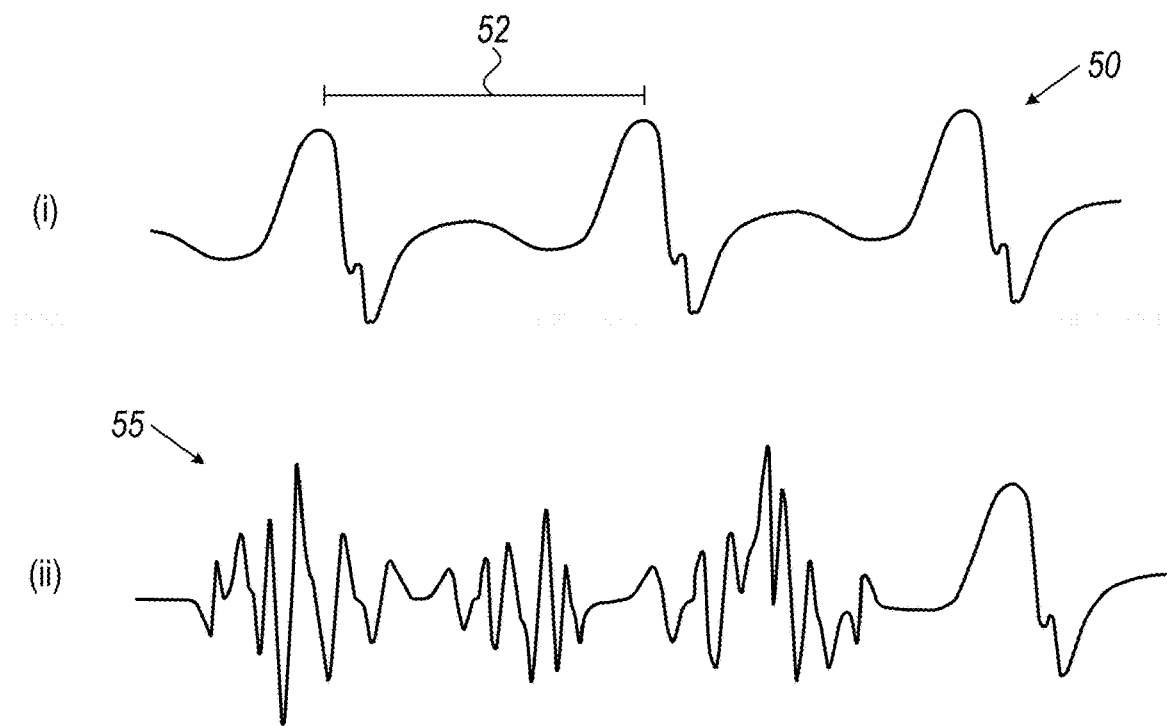
FIG. 2 is a graph showing schematically well-defined vs. fractionated electrogram (EGM) signals, in accordance with an exemplary embodiment of the present invention.

FIG. 2 is a graph showing schematically (i) well-defined 50 vs. (ii) fractionated 55 electrogram (EGM) signals, in accordance with an exemplary embodiment of the present invention. As seen, a well-defined EGM signal enables the definition of a temporal cycle-length 52, whereas at cardiac locations that exhibit fractionated episodes of the EGM signal, a temporal cycle-length cannot be defined. Cardiac locations exhibiting such disrupted EGM signals may be a source of arrhythmogenic activity that requires ablation to treat a resulting arrhythmia. Yet, to complicate things, both cardiac locations that exhibit well-defined cycle lengths and those that present fractionated episodes of the EGM signal have significant clinical value in diagnosing an arrhythmia.

To answer this challenge, exemplary embodiments of the disclosed invention provide graphical techniques to present both types of EP information on the same EP map, such that a physician may more readily analyze and diagnose complex abnormal cardiac activity.

Figure 3:
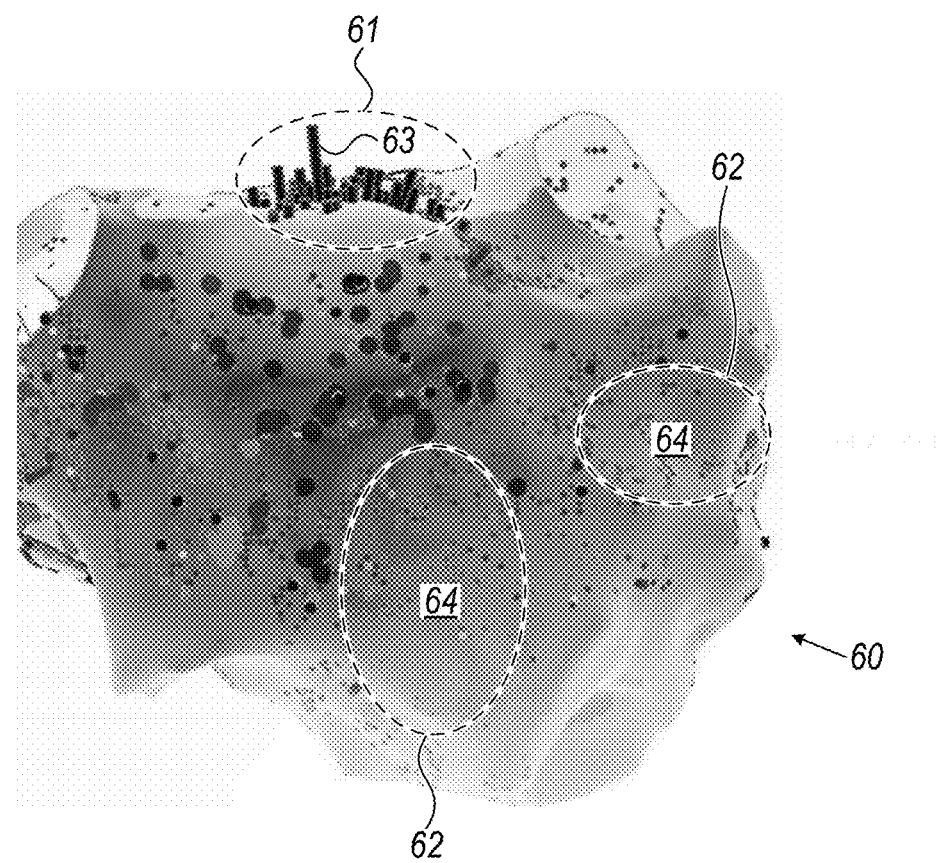
FIG. 3 is a schematic, pictorial volume rendering of a hybrid-representation EP map overlaid on a cardiac chamber anatomy, in accordance with an exemplary embodiment of the present invention.

Propagation Map of a Heart Chamber with Areas Demonstrating Fractionated Electrograms FIG. 3 is a schematic, pictorial volume rendering of a hybrid-representation EP map 60 overlaid on a cardiac chamber anatomy, in accordance with an exemplary embodiment of the present invention. As seen, hybrid-representation EP map 60 comprises a first surface representation 61 of a fractionated area and a second surface representation 62 of non-fractionated (i.e., well-defined) areas.

In areas such as area 61, where temporal analysis is impossible due to the EGM signals being acquired at fractionated surface locations, hybrid-representation EP map 60 provides visualization of fractionated amplitudes overlaid on the anatomy in the form of bars 63 that protrude from the surface, where the height of a bar represents the size of the EGM amplitude at the location at a given time.

The second surface representation 62 encodes propagation-time values, e.g., LAT values, in a form of a color-scale rendering 64 (shown in grey-scale) over areas, such as areas 62, of the anatomical map, where the color of a surface position gives an LAT value at the position at the given time.

Hybrid-representation EP map 60 should be understood as a "snap-shot" of the time-dependent EP activity, and typically, a video mode is used to display hybrid-representation EP map 60.

Figure 4:
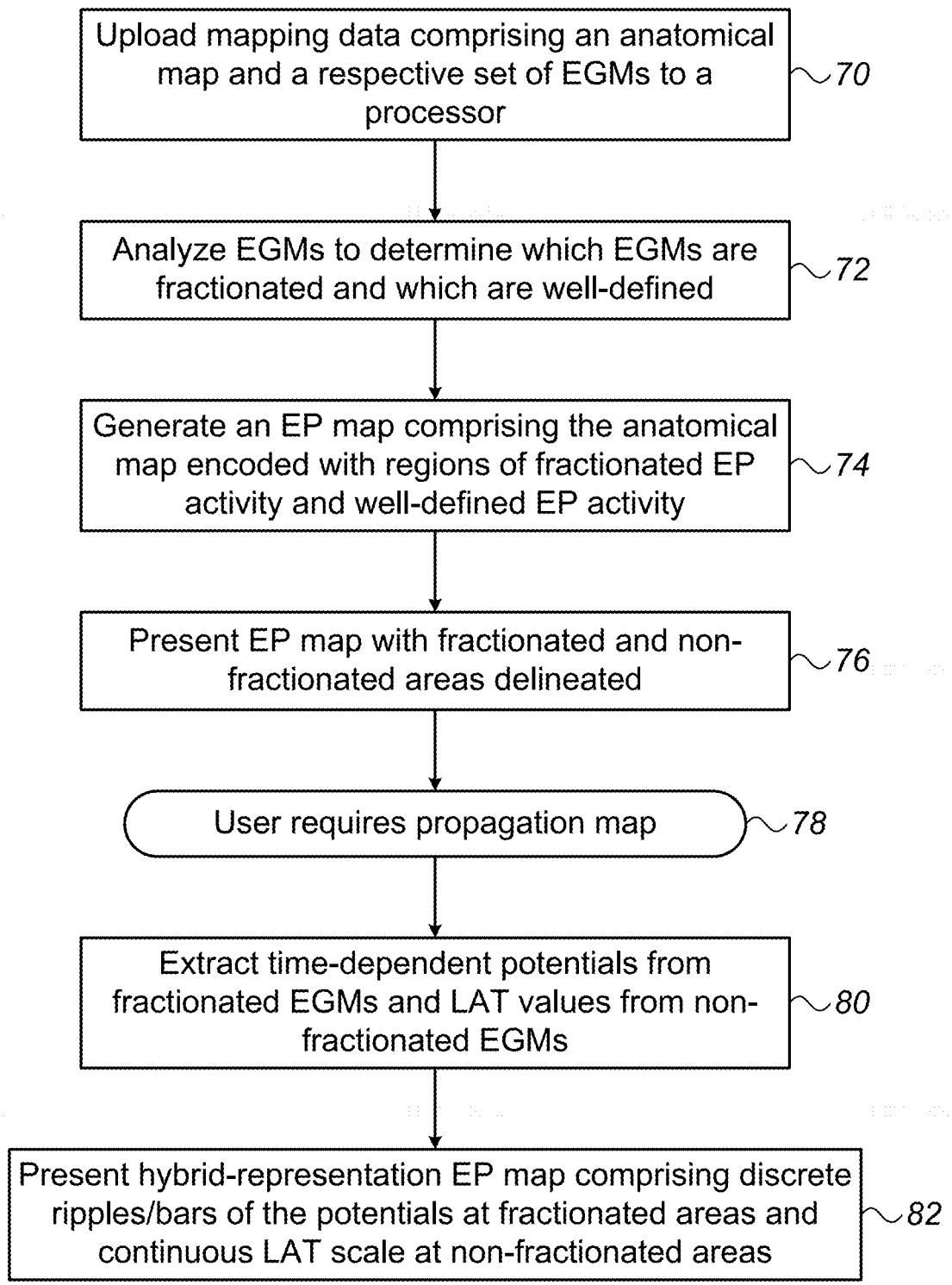
FIG. 4 is flow chart that schematically illustrates a method and algorithm for generating the hybrid-representation EP map of FIG. 3, in accordance with an exemplary embodiment of the present invention.

FIG. 4 is flow chart that schematically illustrates a method and algorithm for generating hybrid representation EP map 60 of FIG. 3, in accordance with an exemplary embodiment of the present invention. The algorithm, according to the presented exemplary embodiment, carries out a process that begins with processor 40 uploading an anatomical map of a cardiac chamber, and EP mapping data (e.g., set of EGMs from surface positions over the mapped anatomy) from memory 44, at an anatomy and EP data uploading step 70.

Next, at an EGM analysis step 72, processor 40 determines which of the uploaded EGMs are fractionated and which are well-defined (e.g., non-fractionated).

At an EP map generation step 74, processor 40 generates an EP map comprising an anatomical map encoded with one or more first regions of fractionated EP activity and one or more second regions of well-defined EP activity and delineate the different regions over the anatomy.

At an EP map presentation step 76, processor 40 presents to a user, e.g., to physician 28 on display 48, the delineated EP map of step 74. At this point, physician 28 may require more information, such as to display a propagation map comprising LAT values or cycle-lengths, at a propagation map requesting step 78.

In order to keep the fractionated EP activity information without obscuring the propagation information, processor 40 derives the aforementioned hybrid-representation EP map 60.

At an EP data analysis step 80, processor 40 extracts signal amplitudes from the fractionated EGMs, and extracts amplitude propagation times, such as LAT values or cycle-lengths, from the non-fractionated EGM signal. Finally, processor 40 constructs the hybrid-representation EP map 60, in which parts of the anatomy are overlaid with a discrete representation (e.g., protruding bars 68) to show the fractionated EP activity, while other parts of the anatomy are overlaid with continuous temporal information of the well-defined EP activity, (e.g., color-scaled areas 64) at step 82.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for characterizing cardiac arrhythmia, the method comprising:
   storing an anatomical map of at least a portion of a surface of a heart;
   storing respective electrogram (EGM) signal amplitudes measured at respective positions on the surface of the heart;
   defining, based on the on the EGM signal amplitudes, one or more first regions of the surface in which the EGM signal amplitudes are fractionated, and one or more second regions of the surface in which the EGM signal amplitudes are non-fractionated;
   generating a first surface representation for the fractionated EGM signal amplitudes in the first regions;
   extracting propagation times from the non-fractionated EGM signal amplitudes in the second regions, and deriving a second surface representation of the propagation times; and
   simultaneously presenting the first and second surface representations of the respective first and second regions of the surface, overlaid on the anatomical map.

2. The method according to claim 1, and comprising generating a third surface representation, for signals which are neither defined as fractionated, nor definable in terms of a propagation time.

3. The method according to claim 1, wherein generating the first surface representation for the fractionated EGM signal amplitudes comprises selecting a subset of the fractionated EGM signal amplitudes and generating the surface for the subset.

4. The method according to claim 1, wherein the first surface representation comprises a geometric shape protruding from the surface.

5. The method according to claim 4, wherein the protruding geometric shape comprises one of ripples and bars.

6. The method according to claim 1, wherein the second surface representation comprises a color scale.

7. The method according to claim 1, wherein the propagation times comprise local activation time (LAT) values.

8. The method according to claim 1, and comprising assigning a local activation time (LAT) value to an EGM signal even though the EGM signal is fractionated, and generating for the fractionated EGM signal a third surface representation that visualizes the third surface representation.

9. The method according to claim 1, wherein the propagation times comprise cycle-length values.

10. A system for characterizing cardiac arrhythmia, the system comprising:
- a memory, which is configured to:
  - store an anatomical map of at least a portion of a surface of a heart; and
  - store respective electrogram (EGM) signal amplitudes measured at respective positions on the surface of the heart; and
- a processor, which is configured to:
  - define, based on the on the EGM signal amplitudes, one or more first regions of the surface in which the EGM signal amplitudes are fractionated, and one or more second regions of the surface in which the EGM signal amplitudes are non-fractionated;
  - generate a first surface representation for the fractionated EGM signal amplitudes in the first regions;
  - extract propagation times from the non-fractionated EGM signal amplitudes in the second regions, and derive a second surface representation of the propagation times; and
  - simultaneously present the first and second surface representations of the respective first and second regions of the surface, overlaid on the anatomical map.

11. The system according to claim 10, wherein the processor is further configured to generate a third surface representation, for signals which are neither defined as fractionated, nor definable in terms of a propagation time.

12. The system according to claim 10, wherein the processor is configured to generate the first surface representation for the fractionated EGM signal amplitudes comprises selecting a subset of the fractionated EGM signal amplitudes and generating the surface for the subset.

13. The system according to claim 10, wherein the first surface representation comprises a geometric shape protruding from the surface.

14. The system according to claim 13, wherein the protruding geometric shape comprises one of ripples and bars.

15. The system according to claim 10, wherein the second surface representation comprises a color scale.

16. The system according to claim 10, wherein the propagation times comprise local activation time (LAT) values.

17. The system according to claim 10, wherein the processor is configured to assign a local activation time (LAT) value to an EGM signal even though the EGM signal is fractionated, and generate for the fractionated EGM signal a third surface representation that visualizes the third surface representation.

18. The system according to claim 10, wherein the propagation times comprise cycle-length values.

* * * * *